US009022925B2

(12) United States Patent
Nan

(10) Patent No.: US 9,022,925 B2
(45) Date of Patent: May 5, 2015

(54) MASSAGE APPARATUS HAVING A SLEEVE WITH A LUBRICATION WELL

(71) Applicant: Nanma Manufacturing Co., Ltd., Hong Kong (CN)

(72) Inventor: Simon Siu Man Nan, Richmond Hill (CA)

(73) Assignee: Nanma Manufacturing Co., Ltd., Hong Kong (HK)

(*) Notice: Subject to any disclaimer, the term of this patent is extended or adjusted under 35 U.S.C. 154(b) by 262 days.

(21) Appl. No.: 13/628,475

(22) Filed: Sep. 27, 2012

(65) Prior Publication Data

US 2014/0088350 A1 Mar. 27, 2014

(51) Int. Cl.

*A61F 5/00* (2006.01)
*A61H 19/00* (2006.01)
*A61H 1/00* (2006.01)
*A61H 23/02* (2006.01)

(52) U.S. Cl.

CPC ................ *A61H 19/34* (2013.01); *A61H 1/005* (2013.01); *Y10T 29/49* (2015.01); *A61H 2201/0153* (2013.01); *A61H 19/44* (2013.01); *A61H 23/0254* (2013.01); *A61H 23/0263* (2013.01); *A61H 2201/105* (2013.01)

(58) Field of Classification Search

CPC .......... A61H 7/00; A61H 19/00; A61H 23/00
USPC ...................................................... 600/38–41
See application file for complete search history.

(56) References Cited

U.S. PATENT DOCUMENTS

| | | | | |
|---|---|---|---|---|
| 5,690,603 | A * | 11/1997 | Kain | 600/38 |
| 6,749,557 | B2 | 6/2004 | Garland | |
| 7,699,795 | B2 | 4/2010 | Nan | |
| 8,308,667 | B2 * | 11/2012 | Lee | 601/46 |
| 2004/0044328 | A1 | 3/2004 | Kemp et al. | |
| 2006/0206000 | A1 | 9/2006 | Gloth | |
| 2008/0119767 | A1 * | 5/2008 | Berry et al. | 601/46 |
| 2012/0215141 | A1 * | 8/2012 | Peddicord | 601/46 |
| 2013/0261385 | A1 * | 10/2013 | Zipper | 600/38 |

* cited by examiner

*Primary Examiner* — John Lacyk
(74) *Attorney, Agent, or Firm* — Polsinelli PC

(57) ABSTRACT

A massage apparatus having a vibrator device engaged to a flexible hollow sleeve that defines a lubrication well for receiving and dispensing a lubricant is disclosed. The lubrication well includes a peripheral wall that defines a well portion configured to receive the lubricant and a protrusion that extends outwardly from the well portion for stimulating the clitoral area of a female individual while facilitating the dispensation of the lubricant from the well portion to that same area.

17 Claims, 4 Drawing Sheets

MASSAGE APPARATUS HAVING A SLEEVE WITH A LUBRICATION WELL

FIELD

This document relates to massage apparatuses, and in particular to massage apparatuses having a vibrator device engaged to a flexible sleeve that defines an external lubrication well for receiving and dispensing a lubricant.

BACKGROUND

Massage apparatuses are used as marital aid devices to promote healthy sexual relationships between partners. In particular, massage apparatuses may have flexible hollow sleeves that have different shapes and configurations for encasing a vibrator device that vibrates the flexible hollow sleeve during operation. However, further improvements in massage apparatuses having a flexible sleeve are desired. Specifically, further improvements in a flexible hollow sleeve that includes a clitoral stimulator that stimulates the clitoral area of a female individual would be desirable.

SUMMARY

In an embodiment, a massage apparatus may include a sleeve having a sleeve body defining a main sleeve body that forms a main chamber and a secondary sleeve body in communication with the main sleeve body that forms a secondary chamber. In addition, a lubrication well is formed on the secondary sleeve body, wherein the lubrication well includes a peripheral wall that defines a well portion configured to receive a lubricant. A vibrator device is disposed within the main chamber and the secondary chamber for generating vibrations that are imparted through the sleeve body.

In another embodiment, a flexible hollow sleeve for use with a vibrator device may include a sleeve having a sleeve body defining a main sleeve body that forms a main chamber and a secondary sleeve body in communication with the main sleeve body that forms a secondary chamber. In addition, a lubrication well is formed on the secondary sleeve body, wherein the lubrication well includes a peripheral wall that defines a well portion configured to receive a lubricant.

In yet another embodiment, a method of using a massage apparatus may include:

- providing a massage apparatus having a vibrator device engaged to a hollow flexible sleeve, wherein the hollow flexible sleeve includes a sleeve body defining a main sleeve body that forms a main chamber and a secondary sleeve body in communication with the main sleeve body that forms a secondary chamber, and a lubrication well formed on the secondary sleeve body, wherein the lubrication well includes a peripheral wall that defines a well portion configured to receive a lubricant;
- dispensing a lubricant within the lubrication well;
- applying the main sleeve body to a vaginal area of a female individual such that the lubrication well is simultaneously in contact with a clitoral area of the female individual; and
- dispensing the lubricant from the lubrication well to the clitoral area of the female individual during contact of the lubrication well to the clitoral area of the female individual.

In one embodiment, a method for manufacturing a massage apparatus may include:

- forming a sleeve having a hollow sleeve body defining a main sleeve body that forms a main chamber and a secondary sleeve body in communication with the main sleeve body that forms a secondary chamber; and
- forming a lubrication well on the secondary sleeve body, wherein the lubrication well includes a peripheral wall that defines a well portion configured to receive a lubricant.

Implementation of the above embodiments may include one or more of the following features:

The main sleeve body may define a head portion and a base portion, while the secondary sleeve body extends outwardly from the base portion of the main sleeve body, and wherein the secondary sleeve body is shorter in length than the main sleeve body, and further wherein the secondary sleeve body may extend outwardly at an angle relative to the main sleeve body.

The lubrication well may further include a protrusion that extends outwardly from the well portion, wherein the protrusion is made from a flexible material that permits the protrusion to vibrate when the vibrator device is made operational and dispense the lubricant from the lubrication well.

The peripheral wall and well portion of the lubrication well collectively define an open enclosure configured to store and dispense the lubricant, wherein the well portion of the lubrication well is oriented to face the main sleeve body.

The method of operating the massage apparatus may include operating the vibrator device such that lubrication well vibrates and dispenses the lubricant from the well portion.

Additional objectives, advantages and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the view of the drawings. The headings used in the figures should not be interpreted to limit the scope of the claims.

DETAILED DESCRIPTION

Figure 1:
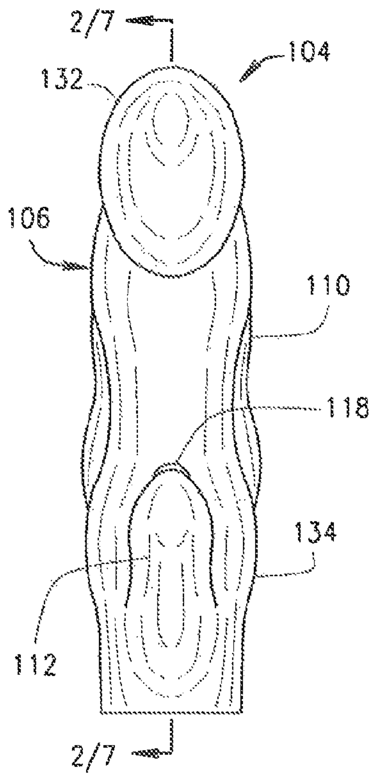
FIG. 1 is a front view of the massage apparatus illustrating a flexible hollow sleeve.
Figure 2:
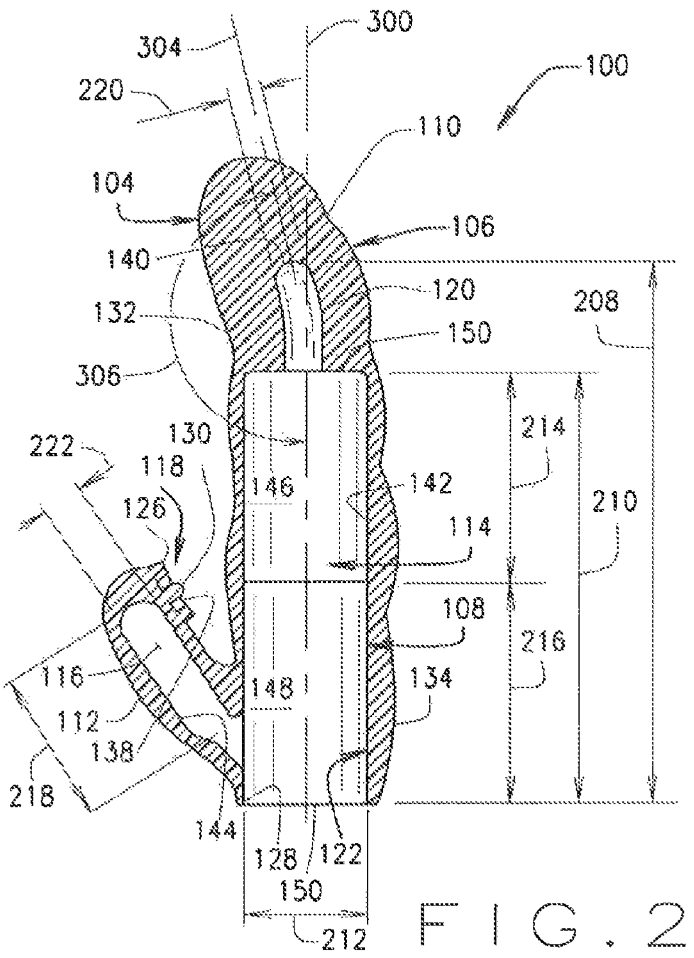
FIG. 2 is a cross-sectional view of the massage apparatus taken along line 2-2 of FIG. 1 illustrating the vibrator device engaged to the flexible hollow sleeve.
Figure 3:
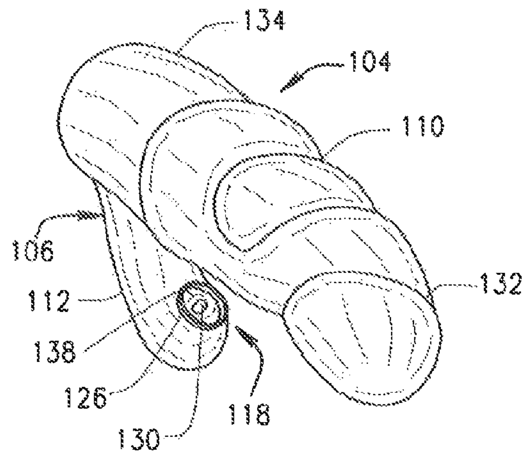
FIG. 3 is an elevated perspective view of the flexible hollow sleeve in a first orientation.
Figure 6:
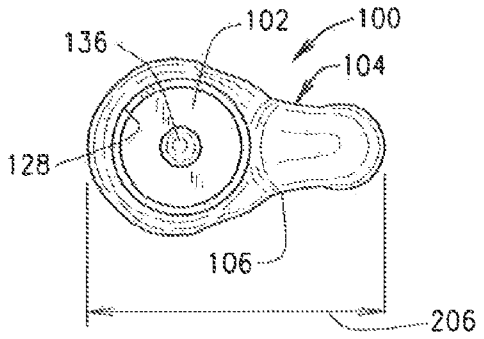
FIG. 6 is an end view of the massage apparatus.
Figure 4:
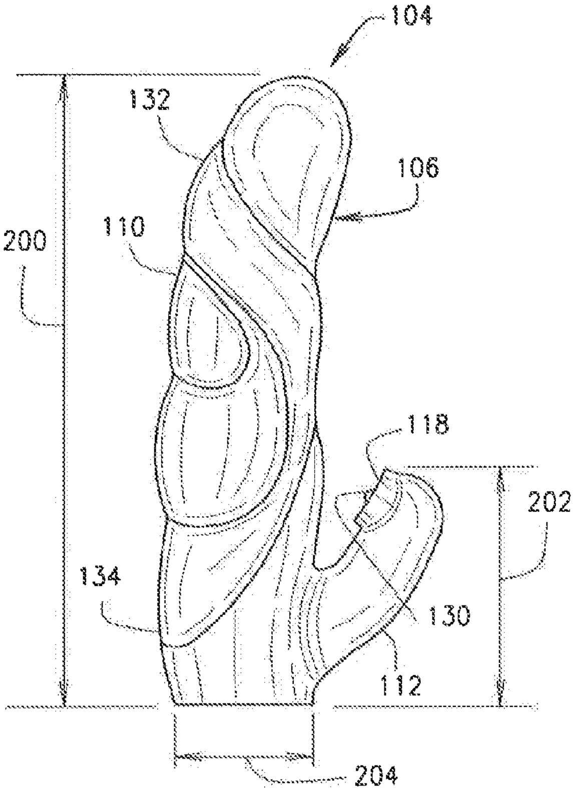
FIG. 4 is a side view of the flexible hollow sleeve.
Figure 7:
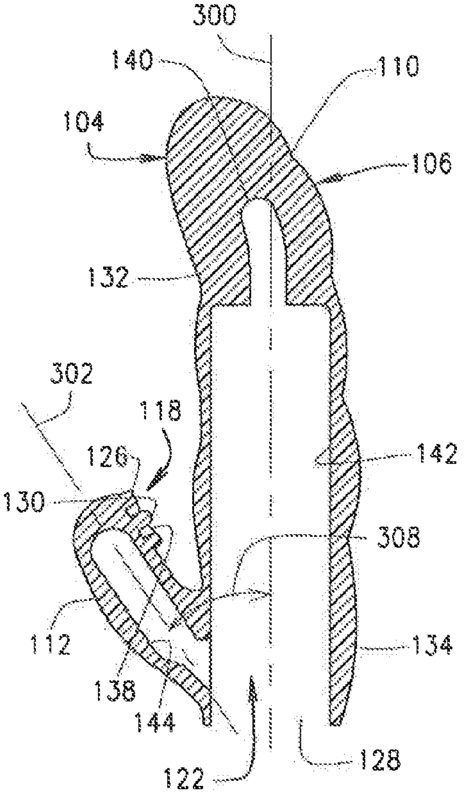
FIG. 7 is a cross-sectional view of the flexible hollow sleeve taken along line 7-7 of FIG. 1 illustrating the chamber of the flexible hollow sleeve.
Figure 5:
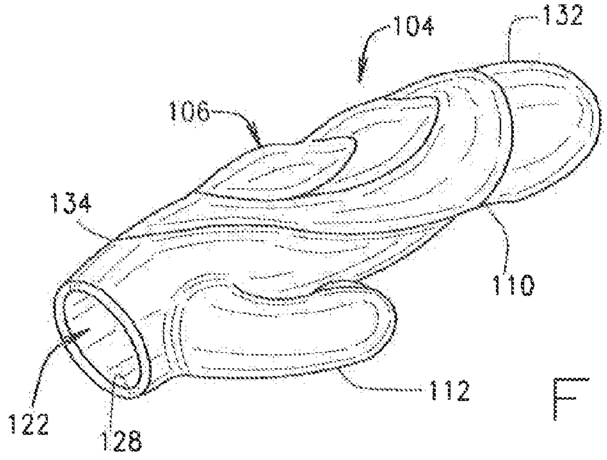
FIG. 5 is an elevated perspective view of the flexible hollow sleeve in a second orientation.
Figure 8:
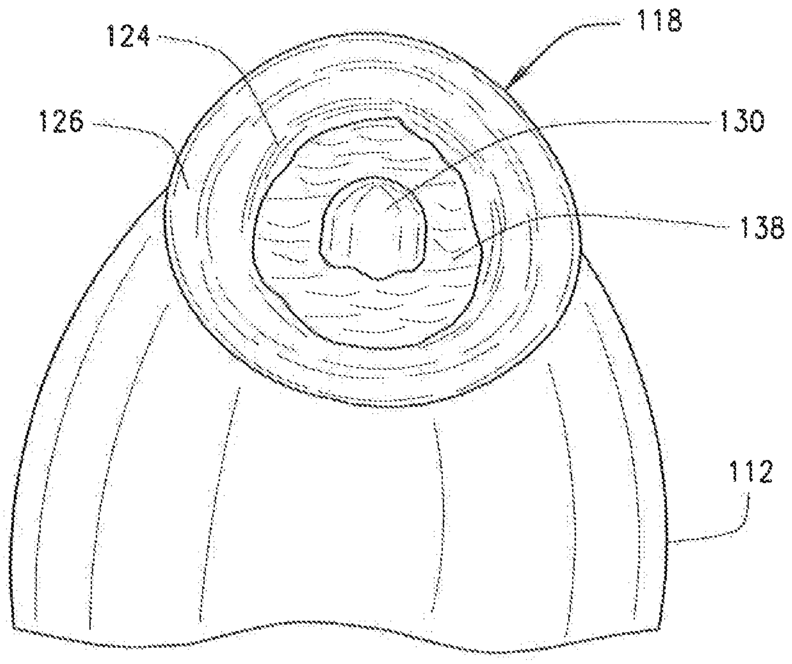
FIG. 8 is an enlarged perspective view of the lubrication well.
Figure 9:
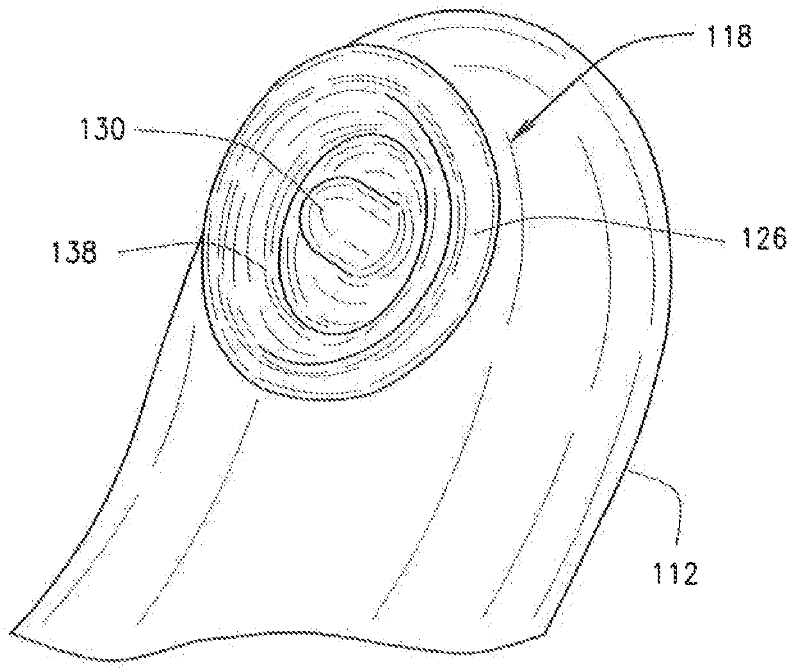
FIG. 9 is another enlarged perspective view of the lubrication well.

Referring to the drawings, an embodiment of the massage apparatus is illustrated and generally indicated as 100 in FIGS. 1-7. Referring to FIGS. 1 and 2, in some embodiments the massage apparatus 100 includes a vibrator device 102 engaged to a flexible hollow sleeve 104. In particular, the flexible hollow sleeve 104 includes a sleeve body 106 that defines a chamber 122 in which the sleeve body 106 has a main sleeve body 110 in communication with a secondary sleeve body 112. Referring to FIGS. 2, 5 and 6, in some embodiments, the main sleeve body 110 defines a generally elongated phallic-shaped body having an opening 128 in communication with the chamber 122, which forms a main chamber 142 in communication with a secondary chamber 144.

As shown in FIG. 2, in one embodiment the vibrator device 102 may include a first vibrator 114 configured to be disposed within the main chamber 142 and a second vibrator 116 configured to be disposed within the secondary chamber 144 of the secondary sleeve body 112. In some embodiments, the first vibrator 114 may include a battery section 148 having one or more batteries (not shown) that powers a motor section 146 that drives and rotates a vibrator rod 120. In one embodiment, the vibrator rod 120 may define a rod tip 140 oriented along a longitudinal axis 304 that forms an angle 306 relative to the longitudinal axis 300 of the main vibrator body 114. As shown in FIGS. 2 and 6, in some embodiments, activation of the power switch 136 operates the first vibrator 114 of vibrator device 102 causing the motor to rotate the vibrator rod 120 with the angled rod tip 140 which generates vibrations that are imparted through the sleeve body 106 of sleeve 104. In some embodiments, activation of the power switch 136 may also operate the second vibrator 116. In some embodiments, the second vibrator 116 may include a motor (not shown) that rotates a rod attached to an eccentric mass (not shown) such that rotation of the eccentric mass generates vibrations that are communicated through the sleeve body 108, and in particular through the secondary sleeve body 112. In the alternative, the massage apparatus 100 may have power cord that may supply power through a conventional power outlet.

Referring to FIGS. 1-5, in some embodiments the main sleeve body 110 of sleeve 104 may define a head portion 132 in communication with a base portion 134. In some embodiments the secondary sleeve body 112 is configured as a clitoral stimulator that extends at an angle from the base portion 134 along an axis 302 (FIG. 7) such that the secondary sleeve body 112 may be positioned to provide stimulation to the clitoral area of the female individual.

As shown in FIGS. 1-4 and 7-9, the secondary sleeve body 112 of the sleeve body 106 includes lubrication well 118 configured to store and dispense a lubricant 124 (FIG. 8), especially to the clitoral area of a female individual. In some embodiments, the lubrication well 118 may be positioned such that application of the main sleeve body 110 to the vaginal area of a female individual allows the lubrication well 118 of the secondary sleeve body 112 to contact the clitoral area of the female individual. In some embodiments, the lubrication well 118 defines a generally circular or oval-shaped peripheral wall 126 forming a well portion 138 configured to receive a lubricant, such as a jelly or oil-based lubricant 124.

In some embodiments, a protrusion 130 may extend outwardly from the well portion 138 for providing stimulation to the clitoral area during application of the massage apparatus 100 to the female individual. In addition, the protrusion 130 may have different configurations and may be made from a flexible material that vibrates and permits stimulation of the clitoral area of the female individual. For example, the protrusion 130 may have a nub-like configuration with a rounded top portion that extends outwardly from the well portion 138. In some embodiments, the protrusion 130 may act as an applicator for applying the lubricant 124 stored in the lubrication well 118, for example in a swabbing action, to the clitoral area of the female individual during operation of the massage apparatus 100. In some embodiments, the vibration of the secondary sleeve body 112 by the vibrator 102 may facilitate the dispensing and application of the lubricant 124 from the lubricant well 118. Specifically, vibration of the lubrication well 118 as the secondary sleeve body 112 is in contact with the clitoral area of the female individual can facilitate dispensation of the lubricant 124 from the well portion 138 to the clitoral area as well as other parts of the female or male individual's body.

In one embodiment, the massage apparatus 100 may be manufactured to have the dimensions as described below. As shown in FIG. 4, in one embodiment of the sleeve body 106, the main sleeve body 110 may have a length 200 of about 141.65 mm and a width 204 of about 31.00 mm, while the secondary sleeve body 112 may have a length 202 of about 52.84 mm. Referring to FIG. 6, the sleeve body 106 may have a length 206 as measured from one end of the main sleeve body 110 to one end of the secondary vibrator body 112 of about 64.78 mm.

Referring to FIG. 2, the vibrator body 108 may have a length 208 as measured from the rod tip 140 of the vibrating rod 120 to the proximal end 150 of the main vibrator body 114 of about 119.50 mm, while the main vibrator body 108 may have a length 210 as measured between the proximal end 150 to the distal end 152 of the main vibrator body 114 of about 95.50 mm and a width 212 of about 26.50 mm. As further shown, the motor section 146 may have a length 214 of about 43.50 mm and the battery section 148 may have a length 216 of about 52 mm, while the secondary vibrator body 116 may have a length 218 of about 34 mm and a width 222 of about 10 mm. In addition, the vibrating rod 120 may have a width 220 of about 8 mm and may be oriented along a longitudinal axis 304 which forms an angle 306 of about 170 degrees relative to longitudinal axis 300 of the main vibrator body 114. In some embodiments, the angle 306 formed between the longitudinal axes 300 and 304 may range between 90 degrees to 180 degrees.

Figure 10:
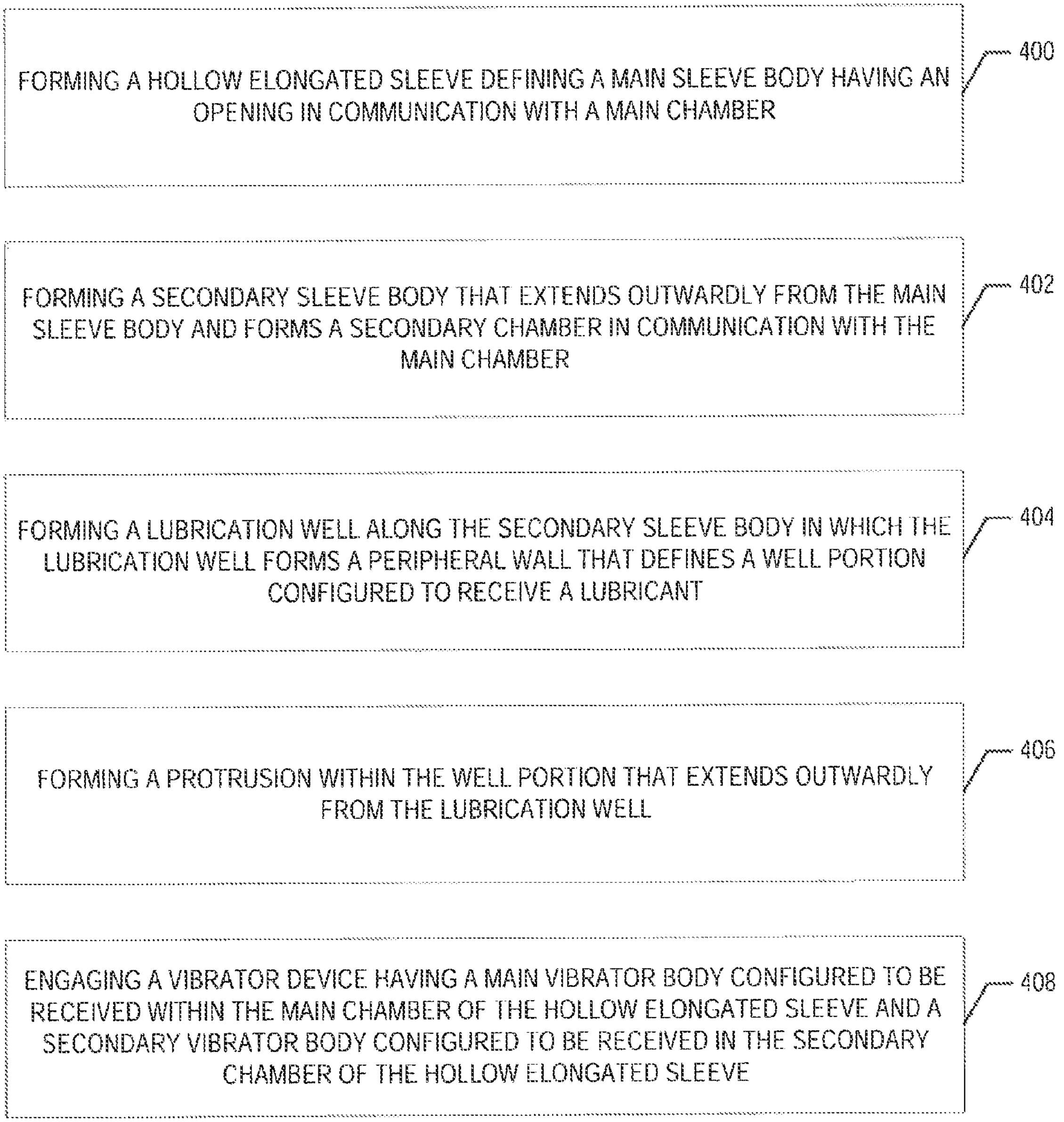
FIG. 10 is a flow chart illustrating a method of manufacturing the massage apparatus.

Referring to FIG. 10, a flow chart illustrates one method for manufacturing an embodiment of the massage apparatus 100. At block 400, forming a hollow elongated sleeve 104 defining a main sleeve body 110 having an opening 128 in communication with a main chamber 142. At block 402, forming a secondary sleeve body 112 that extends outwardly from the main sleeve body 110 and forms a secondary chamber 144 in communication with the main chamber 142. At block 404, forming a lubrication well 118 along the secondary sleeve body 112 in which the lubrication well 118 forms a peripheral wall 126 that defines a well portion 138 configured to receive a lubricant. At block 406, forming a protrusion 130 within the well portion 138 that extends outwardly from the lubrication well 118. At block 408, engaging a vibrator device 102 having a main vibrator body 114 configured to be received in the main chamber 142 of the sleeve 104 and a secondary vibrator body 116 configured to be received in the secondary chamber 144 of the sleeve 104.

During manufacture, the lubrication well 118 may be formed on the secondary sleeve body 112 such that the well portion 138 faces the main sleeve body 110. In this orientation, application of the head portion 132 of the main sleeve body 110 to the vaginal area of the female individual allows the lubrication well 118 to be brought into contact with the clitoral area of the female individual. In some embodiments, activation of the main vibrator body 114 and/or the secondary vibrator body 116 allows the lubricant stored in the lubrication well 118 to be dispensed from the well portion 138 and be applied to the clitoral area, while in other embodiments, the lubricant may be dispensed from the well portion 138 without the vibrator device 102 being made operational.

In some embodiments, the sleeve body 106 may have a substantially elongated configuration having a generally bulbous shape, while in other embodiments the sleeve body 106 may have a smooth shape. In some embodiments, the sleeve body 106 may have a generally curved shape, while in other embodiments the sleeve body 106 may have a generally straight shape or curved. In some embodiments, head portion 132 of the main sleeve body 110 may be bent at an angle relative to the base portion 134. In one embodiment, the secondary sleeve body 112 may extend outwardly from the main sleeve body 110 at a longitudinal axis 302 that forms an angle 308 relative to longitudinal axis 300 of about 45 degrees. In some embodiments, angle 308 may range between 15 degrees to 85 degrees.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A massage apparatus comprising:

a sleeve having a sleeve body defining a main sleeve body that forms a main chamber and a secondary sleeve body in communication with the main sleeve body that forms a secondary chamber;

a lubrication well formed on the secondary sleeve body, wherein the lubrication well includes a continuous peripheral wall that defines a well portion configured to receive a lubricant; and a plurality of vibrator devices disposed within the main chamber and the secondary chamber for generating vibrations that are imparted through the sleeve body.

2. The massage apparatus of claim 1, wherein the secondary sleeve body extends outwardly at an angle relative to the main sleeve body.

3. The massage apparatus of claim 1, wherein the lubrication well further includes a protrusion that extends outwardly from the well portion.

4. The massage apparatus of claim 3, wherein the protrusion is made from a flexible material that permits the protrusion to vibrate when the plurality of vibrator devices is made operational and dispense the lubricant from the lubrication well.

5. The massage apparatus of claim 1, wherein the plurality of vibrator devices comprises a first vibrator disposed in the main chamber and a second vibrator disposed in the secondary chamber.

6. The massage apparatus of claim 5, wherein the second vibrator is positioned proximate to the lubrication well.

7. The massage apparatus of claim 1, wherein the well portion of the lubrication well defines an open enclosure configured to store and dispense the lubricant.

8. The massage apparatus of claim 1, wherein the well portion of the lubrication well is oriented to face the main sleeve body.

9. The massage apparatus of claim 1, wherein the main sleeve body defines a head portion and a base portion, wherein the secondary sleeve body extends outwardly from the base portion of the main sleeve body, and wherein the secondary sleeve body is shorter in length than the main sleeve body.

10. The massage apparatus of claim 1, wherein the peripheral wall of the lubrication well extends outwardly from the secondary sleeve body.

11. A flexible hollow sleeve for use with a vibrator device comprising:

a sleeve having a sleeve body defining a main sleeve body that forms a main chamber and a secondary sleeve body in communication with the main sleeve body that forms a secondary chamber;

a lubrication well formed on the secondary sleeve body, wherein the lubrication well includes a continuous peripheral wall that defines a well portion configured to receive a lubricant.

12. A method of using a massage apparatus comprising:

providing a massage apparatus comprising a vibrator device engaged to a hollow flexible sleeve, wherein the hollow flexible sleeve comprises a sleeve body defining a main sleeve body that forms a main chamber and a secondary sleeve body in communication with the main sleeve body that forms a secondary chamber, and a lubrication well formed on the secondary sleeve body, wherein the lubrication well includes a continuous peripheral wall that defines a well portion configured to receive a lubricant;

disposing a lubricant within the lubrication well;

applying the main sleeve body to a vaginal area of a female individual such that the lubrication well is simultaneously in contact with a clitoral area of the female individual; and dispensing the lubricant from the lubrication well to the clitoral area of the female individual during contact of the lubrication well to the clitoral area of the female individual.

13. The method of claim 12, further comprising:

operating the vibrator device such that lubrication well vibrates and dispenses the lubricant from the well portion of the lubrication well.

14. The method of claim 12, wherein providing the massage apparatus further comprises:

providing a lubrication well having a protrusion that extends outwardly from the well portion such that operation of the vibrator device vibrates the protrusion and facilitates dispensation of the lubricant from the well portion by the protrusion.

15. A method for manufacturing a massage apparatus comprising:

forming a sleeve having a hollow sleeve body defining a main sleeve body that forms a main chamber and a secondary sleeve body in communication with the main sleeve body that forms a secondary chamber; and forming a lubrication well on the secondary sleeve body, wherein the lubrication well includes a continuous peripheral wall that defines a well portion configured to receive a lubricant.

16. The method of claim 15, further comprising:

engaging a vibrator device configured to be received within the sleeve body, wherein the vibrator device comprises a first vibrator configured to be received within the main sleeve body and a second vibrator configured to be received within the secondary sleeve body.

17. The method of claim 15 further comprising:

forming a protrusion that extends outwardly from the well portion of the lubrication well.

* * * * *